United States Patent
Arvidson et al.

(10) Patent No.: US 6,874,713 B2
(45) Date of Patent: Apr. 5, 2005

(54) METHOD AND APPARATUS FOR IMPROVING SILICON PROCESSING EFFICIENCY

(75) Inventors: Arvid Neil Arvidson, Sanford, MI (US); Todd Stanley Graham, Freeland, MI (US); Kathryn Elizabeth Messner, Midland, MI (US); Chris Tim Schmidt, Midland, MI (US); Terence Lee Horstman, Frankenmuth, MI (US)

(73) Assignee: Dow Corning Corporation, Midland, MI (US)

( * ) Notice: Subject to any disclaimer, the term of this patent is extended or adjusted under 35 U.S.C. 154(b) by 133 days.

(21) Appl. No.: 10/227,362

(22) Filed: Aug. 22, 2002

(65) Prior Publication Data

US 2004/0035960 A1 Feb. 26, 2004

(51) Int. Cl.$^7$ .............................................. B02C 19/12
(52) U.S. Cl. ............................ 241/1; 209/2; 209/235; 209/288; 241/23; 241/24.1
(58) Field of Search .......................... 209/2, 235, 288, 209/664; 241/24.1, 30, 23, 1

(56) References Cited

U.S. PATENT DOCUMENTS

| | | | |
|---|---|---|---|
| 4,092,446 A | 5/1978 | Padovani et al. | 427/213 |
| 4,213,937 A | 7/1980 | Padovani et al. | 422/142 |
| 4,565,913 A | 1/1986 | Yatsurugi et al. | 219/10.55 |
| 4,871,117 A | 10/1989 | Baueregger et al. | 241/23 |
| 4,971,654 A | 11/1990 | Burghausen et al. | 156/638 |
| 5,123,636 A | 6/1992 | Dumler et al. | 269/15 |
| 5,165,548 A | 11/1992 | Dumler et al. | 209/2 |
| 5,464,159 A | 11/1995 | Wolf et al. | 241/1 |

(Continued)

FOREIGN PATENT DOCUMENTS

| | | |
|---|---|---|
| CA | 954425 | 9/1974 |
| DE | 39 13 379 A1 | 4/1989 |
| DE | 42 23 458 A1 | 7/1992 |
| DE | 197 49 127 A1 | 6/1999 |
| EP | 0 329 163 B1 | 2/1989 |

(Continued)

OTHER PUBLICATIONS

Semiconductor Silicon Crystal Technology, "Silicon Crystal Growth and Wafer Preparation, " Fumio Shimura, Department of Materials Science and Engineering, North Caroline State University, Raleigh, North Carolina. Academic Press, 1989, pp. 178–213.

(Continued)

*Primary Examiner*—Mark Rosenbaum
(74) *Attorney, Agent, or Firm*—Catherine U. Brown

(57) ABSTRACT

A method for processing polycrystalline silicon workpieces to form size distributions of polycrystalline silicon pieces suitable for use in a Czochralski-type process includes: (1) preparing a polycrystalline silicon workpiece by a chemical vapor deposition process; (2) fracturing the polycrystalline silicon workpiece into a mixture of polycrystalline silicon pieces, where the polycrystalline silicon pieces have varying sizes; and (3) sorting the mixture of polycrystalline silicon pieces into at least two size distributions. Step (2) may be carried out by a thermal shock process. Step (3) may be carried out using a rotary indent classifier. A rotary indent classifier for performing the method includes: (i) a rotating cylinder having a circumferential edge with indents arrayed in increasing size from a first end of the cylinder to a second end of the cylinder, and (ii) a conveyor running longitudinally adjacent the cylinder, for conveying silicon pieces from the first end of the cylinder to the second end of the cylinder.

31 Claims, 6 Drawing Sheets

U.S. PATENT DOCUMENTS

| | | | |
|---|---|---|---|
| 5,660,335 A | 8/1997 | Koppl et al. .................... | 241/1 |
| 5,753,567 A | 5/1998 | Banan et al. ................ | 438/720 |
| 5,791,493 A | 8/1998 | Meyer ......................... | 209/245 |
| 5,820,688 A | 10/1998 | Koppl et al. .................... | 134/2 |
| 5,851,303 A | 12/1998 | Hwang et al. ................. | 134/3 |
| 5,976,481 A | 11/1999 | Kubota et al. ............. | 423/348 |
| 6,024,306 A | 2/2000 | Koppl et al. .................... | 241/1 |
| 6,063,697 A | 5/2000 | Wolf et al. ................. | 438/472 |
| 6,284,040 B1 | 9/2001 | Holder et al. ................. | 117/13 |
| 6,309,467 B1 | 10/2001 | Wochner et al. ............... | 134/2 |
| 6,313,013 B1 | 11/2001 | Flottmann et al. .......... | 438/472 |
| 6,375,011 B1 | 4/2002 | Flottmann et al. .......... | 209/261 |
| 2003/0041795 A1 | 3/2003 | Moroishi et al. ............. | 117/13 |

FOREIGN PATENT DOCUMENTS

| | | |
|---|---|---|
| EP | 0 539 097 A1 | 10/1992 |
| GB | 1 368 224 | 2/1973 |
| JP | 63-287565 | 11/1988 |
| JP | 64-014109 | 1/1989 |
| JP | 2-152554 | 6/1990 |
| JP | 7-61808 | 8/1993 |
| JP | 6-271309 | 9/1994 |
| JP | 10-15422 | 1/1998 |
| JP | 11-169795 | 6/1999 |
| JP | 11-290712 | 10/1999 |
| WO | WO 01/61070 A1 | 8/2000 |

OTHER PUBLICATIONS

U.S. Department of Energy, "Advanced Czochralski Silicon Growth Technology for Photovoltaic Modules," DOE/JPL–1012–70 (DE83002206) Flat Plate Solar Array Project, Taher Daud and Akaram H. Kachare, Sep. 15, 1982.

Product data sheet; Carter Day No. 3Si Uniflow Product Flow Configuration, Total pp.: 3.

Product data sheet; Carter Day Disc Separation Principles. Total pp.: 3.

Product data sheet; Carter Day Trommel. Total pp.: 3.

Product data sheet; Carter Day Cylinder Configuration. Total pp.: 2.

Product data sheet; Key Technologies Inc. Rotary Size Grader. Total pp.: 2.

Product data sheets; Fielder's Choice Direct; Gravity Table, Shape Separation, Length Grader, Size Separation and Aspirator. Total sheets: 5.

"Handbook of Semiconductor Silicon Technology," edited by William C. O'Mara, Robert B. Herring and Lee P. Hunt, Noyes Publications, Park Ridge, New Jersey, USA, 1990, Ch. 2, pp. 39–58.

METHOD AND APPARATUS FOR IMPROVING SILICON PROCESSING EFFICIENCY

FIELD OF THE INVENTION

The mixture of polycrystalline silicon pieces of varying sizes may be sorted into at least two size distributions by a variety of methods. The mixture may be sorted by hand or by machine. For example, the mixture of polycrystalline silicon pieces may be sorted using methods and apparatuses known in the art, such as the rotary silicon screen disclosed in U.S. Pat. No. 5,165,548. Alternatively, the mixture may be fed to a rotary indent classifier that sorts the mixture into at least two size distributions. The mixture may be fed to the classifier by any convenient means, such as a hopper, a chute, or a conveyor such as a bucket, belt, or vibratory conveyor.

BACKGROUND OF THE INVENTION

Polycrystalline silicon may be prepared using a chemical vapor deposition (CVD) process in a cold wall bell jar reactor. Typically, this process is produced by CVD of a high purity silane or chlorosilane onto a heated substrate. The resulting product is a polycrystalline silicon workpiece such as a rod or ribbon. Polycrystalline silicon may be used to form monocrystalline silicon. Most semiconductor chips used in electronic devices are fabricated from monocrystalline silicon prepared by a Czochralski-type (CZ) process. In the CZ process, a monocrystalline silicon ingot is produced by melting polycrystalline silicon source material in a quartz crucible, stabilizing the crucible and source melt at an equilibrium temperature, dipping a seed crystal into the source melt, withdrawing the seed crystal as the source melt crystallizes on the seed to form a single crystal ingot, and pulling the ingot as it grows. Melting occurs at a temperature of 1412° C. to 1420° C. in an inert gas environment at low absolute pressure. The crucible is continually rotated about a generally vertical axis as the crystal grows. The rate at which the ingot is pulled from the source melt is selected to form an ingot having a desired diameter.

However, polycrystalline silicon workpieces are usually processed before they may be used to form monocrystalline silicon in the CZ process. The polycrystalline silicon workpieces are usually broken into pieces suitably sized for loading in the crucible. Mixtures of silicon pieces with different size distributions may be used to maximize the charge loaded in the crucible.

One method by which polycrystalline silicon workpieces are processed is a hand processing method. Operators in a clean room environment place the polycrystalline silicon workpieces on a low-contaminate work surface and strike the polycrystalline silicon workpieces with a low contamination impact tool to form polycrystalline silicon pieces.

The operators then manually sort the polycrystalline silicon pieces into at least two size distributions and package the sorted polycrystalline silicon pieces into high-purity bags. This process suffers from the drawbacks of being labor intensive and costly. Furthermore, this process suffers from the drawback that each operator may break and sort pieces somewhat differently, so the resulting product may differ in size distribution from operator to operator. Therefore, there is a continuing need for improved methods for preparing and sorting polycrystalline silicon pieces.

SUMMARY OF THE INVENTION

This invention relates to a method and apparatus for processing silicon. While the invention described below is described in detail with respect to polycrystalline silicon, one skilled in the art would recognize that the method and apparatus described herein may be used for polycrystalline silicon or monocrystalline silicon, or combinations thereof.

BRIEF DESCRIPTION OF THE DRAWINGS

FIG. 1a is an end view of the assembly 100 in FIG. 1.

DETAILED DESCRIPTION OF THE INVENTION

Figure 1:
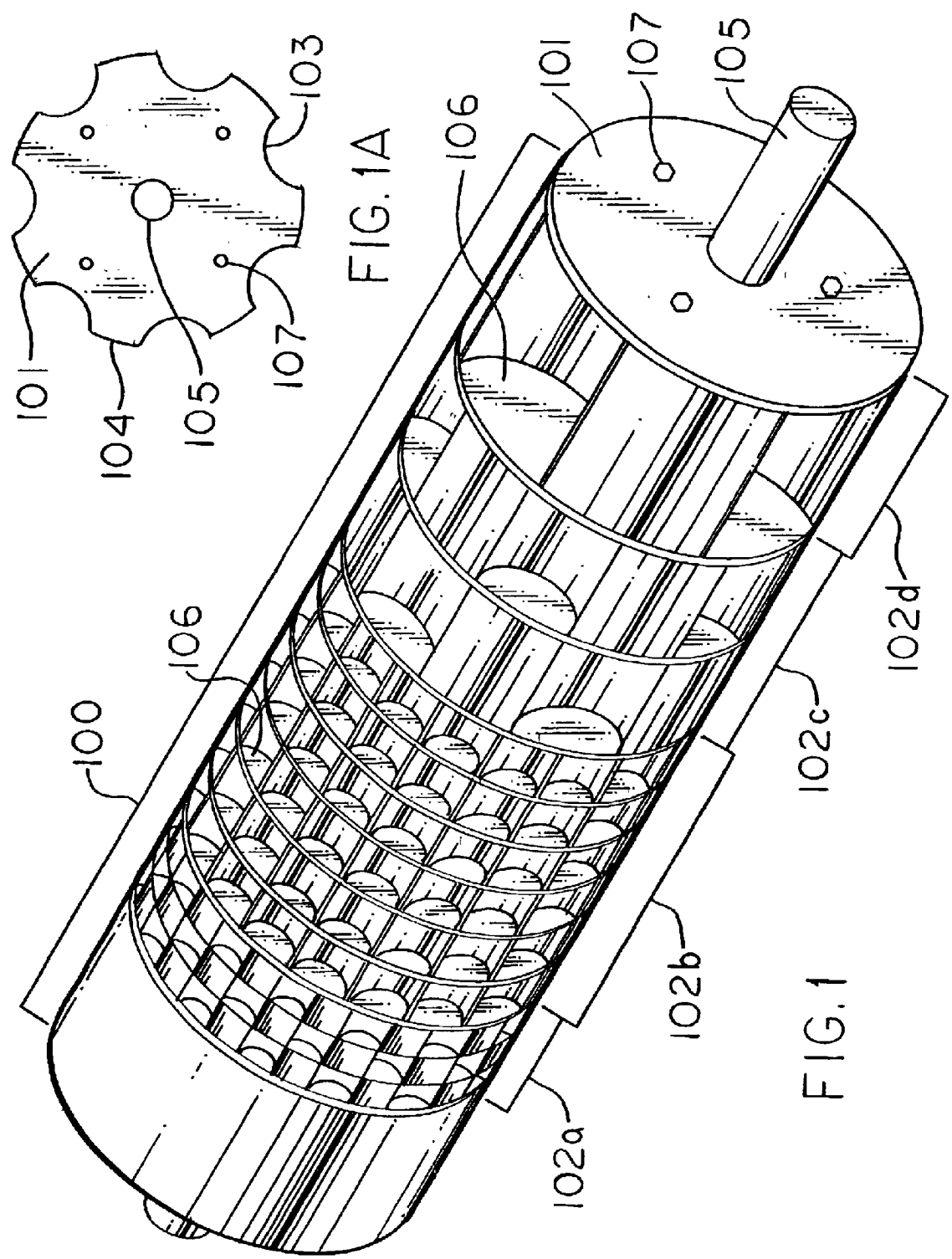
FIG. 1 is a three-dimensional view of an assembly 100 comprising a plurality of indent disks 102 for use in a rotary indent classifier according to this invention.

All amounts, ratios, and percentages are by weight unless otherwise indicated. The following is a list of definitions, as used herein.

Definitions and Usage of Terms

"A" and "an" each mean one or more.

"Combination" means two or more items put together by any method.

The abbreviation "° C." means degrees Celsius.

The abbreviation "° F." means degrees Fahrenheit.

The abbreviation "K" means Kelvin.

The abbreviation "Kg" means kilograms.

The abbreviation "mm" means millimeters.

The abbreviation "m/s" means meters per second.

"Particle size" means the longest straight line between two points on a particle. For example, for spherical particles, particle size is the diameter.

The abbreviation "r.p.m." means revolutions per minute.

Method of the Invention

This invention relates to a method for processing polycrystalline silicon. The method comprises preparing different size distributions of polycrystalline silicon pieces, which are suitable for use in a CZ process. The method may comprise preparing a polycrystalline silicon workpiece by a chemical vapor deposition process, fracturing the polycrystalline silicon workpiece into a mixture of polycrystalline silicon pieces of varying sizes, and sorting the mixture of polycrystalline silicon pieces having varying sizes into at least two size distributions. The polycrystalline silicon workpiece may be fractured by a thermal shock process. Alternatively, the method may comprise preparing a mixture of polycrystalline silicon pieces of varying sizes using a fluidized bed reactor process and sorting the mixture of polycrystalline silicon pieces of varying sizes into at least two size distributions. In the method of this invention, a mixture of polycrystalline silicon pieces having varying sizes prepared by either the chemical vapor deposition process or the fluidized bed reactor process may be sorted using a rotary indent classifier, such as the rotary indent classifier of this invention.

Preparing Polycrystalline Silicon Workpieces

Polycrystalline silicon workpieces that may be used in the method described herein include rods and ribbons that may be prepared by methods known in the art. For example, polycrystalline silicon rods may be prepared by a chemical vapor deposition process comprising chemical vapor deposition of a high purity chlorosilane or silane gas onto a heated substrate, see *Handbook of Semiconductor Silicon Technology,* edited by William C. O'Mara, Robert B. Herring, and Lee P. Hunt, Noyes Publications, Park Ridge, N.J., U.S.A., 1990, Ch. 2, pp. 39–58.

Alternatively, polycrystalline silicon ribbons may be prepared by a chemical vapor deposition process as described by Chandra, et al., in WO 01/61070 A1.

Alternatively, polycrystalline silicon workpieces may be prepared by a fluidized bed reactor process, such as those described by U.S. Pat. Nos. 4,092,446 and 4,213,937. The polycrystalline silicon workpieces prepared by the fluidized bed reactor process may be suitably sized to be sorted into size distributions by the methods and apparatuses described below (e.g., the fluidized bed reactor process may directly produce a mixture of polycrystalline silicon pieces of varying sizes that do not require fracturing before sorting).

Polycrystalline silicon workpieces that are not suitably sized to be sorted may be fractured to prepare a mixture of polycrystalline silicon pieces of varying sizes, where the sizes are suitable for sorting by the methods and apparatus described below.

Fracturing Polycrystalline Silicon Workpieces

The polycrystalline silicon workpieces may be fractured, for example, by striking with a low-contamination impact tool such as that disclosed in EP 0 539 097 A1. Alternatively the polycrystalline silicon workpieces may be fractured by a thermal shock process such as those disclosed in GB 1 368 224 and EP 0 329 163 B1.

Alternatively, the polycrystalline silicon workpieces may be fractured by a thermal shock process comprising controlled heating and cooling of the polycrystalline silicon workpiece thereby generating stress cracks throughout the polycrystalline silicon workpiece. A separator may be used to extend the cracks and reduce the polycrystalline silicon workpiece to a mixture of polycrystalline silicon pieces of varying sizes.

In the thermal shock process, the polycrystalline silicon workpiece is heated to a predetermined temperature, and the heated polycrystalline silicon workpiece is cooled with a fluid spray. The polycrystalline silicon workpiece may be heated to a temperature of 600 to 1400° F., alternatively 1200 to 1400° F., alternatively 600 to 750° F., alternatively 630 to 750° F., alternatively 650 to 700° F. The polycrystalline silicon workpiece may be heated by, for example, laser, infra-red, or microwave energy. Methods and apparatuses for heating the polycrystalline silicon workpiece include, for example, those disclosed in JP 63-287565, and U.S. Pat. Nos. 4,565,913 and 5,464,159.

Figure 8:
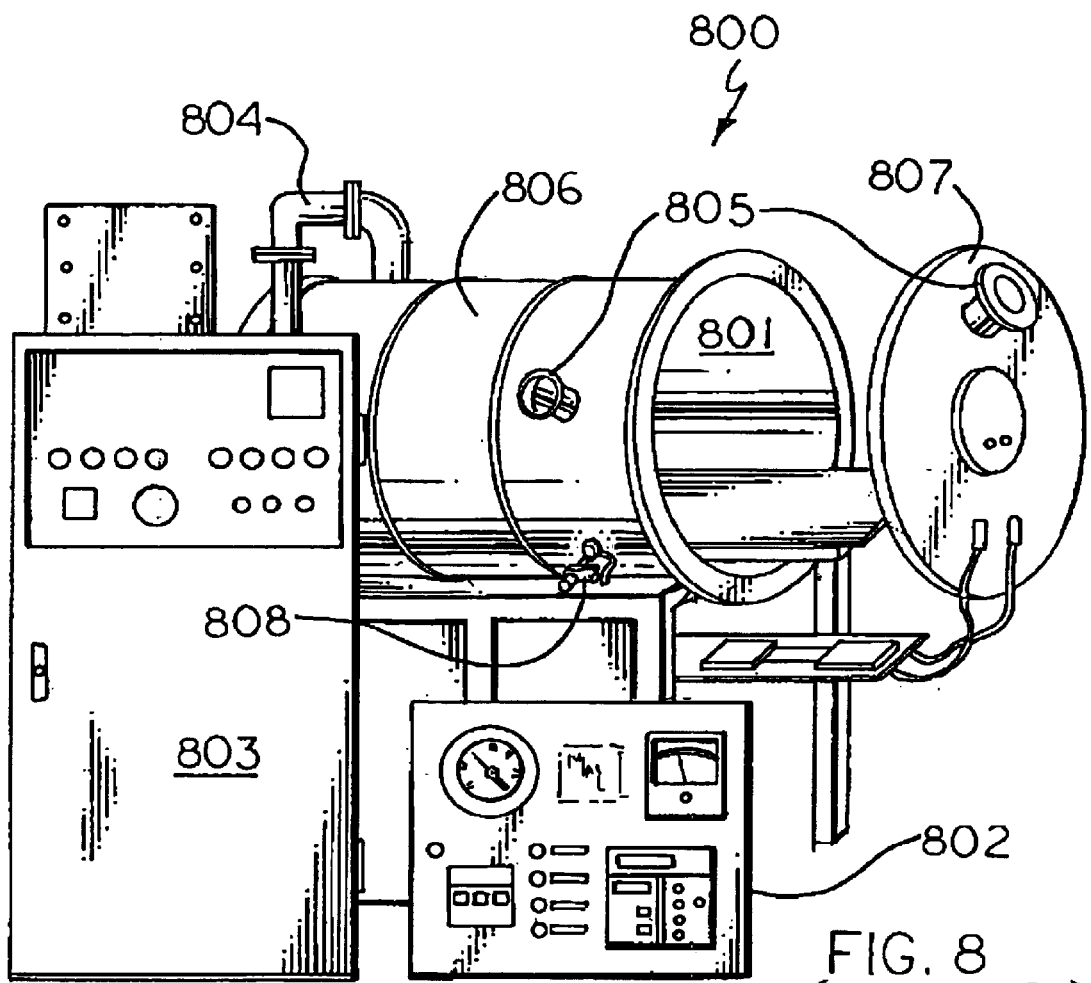
FIG. 8 is a controlled atmosphere microwave furnace for heating polycrystalline silicon workpieces.

Apparatuses for heating are known in the art and are commercially available. For example, a suitable controlled atmosphere microwave furnace for heating polycrystalline silicon is shown in FIG. 8 and is commercially available from Microwave Materials Technologies, Inc., of Oak Ridge, Tenn., U.S.A. (Model 101). The controlled atmosphere microwave furnace 800 includes a controlled atmosphere chamber 801 electrically connected to a control cabinet 802 for controlling the temperature inside the chamber 801. A microwave supply 803 supplies microwave energy to the chamber 801 through a waveguide assembly 804. The chamber 801 has viewports 805 in the side 806 and in the door 807. A thermocouple 808 may be used to measure temperature inside the chamber 801.

The heated polycrystalline silicon workpiece may be cooled using various high-purity fluids, e.g., a gas or a liquid. Suitable gases comprise air, inert gases such as nitrogen, or combinations thereof. Suitable liquids comprise water or a liquefied inert gas. When water is used, deionized, distilled, or otherwise purified water may be used to minimize contamination of the silicon with impurities that are undesirable to customers. Alternatively, solutions of HF or ammonium hydroxide in water may be used.

The fluid may be sprayed on the heated polycrystalline silicon workpiece from a nozzle, alternatively a plurality of nozzles. The size and shape of the silicon pieces generated tends to depend on type of nozzles, the position and orientation of the nozzles, and the fluid flow rate. The spacing of nozzles tends to affect size distribution of the mixture of silicon pieces formed. The nozzles may be spaced 1 to 6 inches apart, alternatively 2 to 4 inches apart to produce desirable size pieces. Nozzle orientation tends to influence the shape of the silicon pieces. A flat fan and a tube nozzle oriented perpendicular to the axis of the workpiece tend to produce irregular shaped pieces. An axial orientation tends to produce uniform wedge or pie shaped pieces. The type of nozzle and spray pattern tend to influence the shape of the pieces. A cone spray pattern tends to produce a number of semicircular pieces. A flat fan spray tends to produce wedge shaped pieces. One skilled in the art would recognize that the size distribution and shape of the pieces also tend to be influenced by the process used to make the polycrystalline silicon workpiece and the internal stresses created thereby. One skilled in the art would be able to select nozzle types and orientations without undue experimentation.

The fluid is sprayed so as to create enough stress to crack the polycrystalline silicon workpiece. The velocity of the fluid to be used depends on the method of making the polycrystalline silicon workpiece and the internal stresses created thereby, the type of the fluid to be used, the temperature of the fluid to be used, and the temperature of the workpiece. For example, when air at ambient temperature is used as the fluid, velocity may be greater than 60 m/s for polycrystalline silicon workpieces made by Hemlock Semiconductor Corporation and heated to 973 K. When air at ambient temperature is used as the fluid, velocity is greater than 130 m/s for polycrystalline silicon workpieces made by Hemlock Semiconductor Corporation and heated to 873 K. When water at ambient temperature is used as the fluid, velocity is greater than 1 m/s for polycrystalline silicon workpieces at 973 K. When water at ambient temperature is used as the fluid, velocity is greater than 2.5 m/s for polycrystalline silicon workpieces made by Hemlock Semiconductor Corporation and heated to 873 K.

Figure 9:
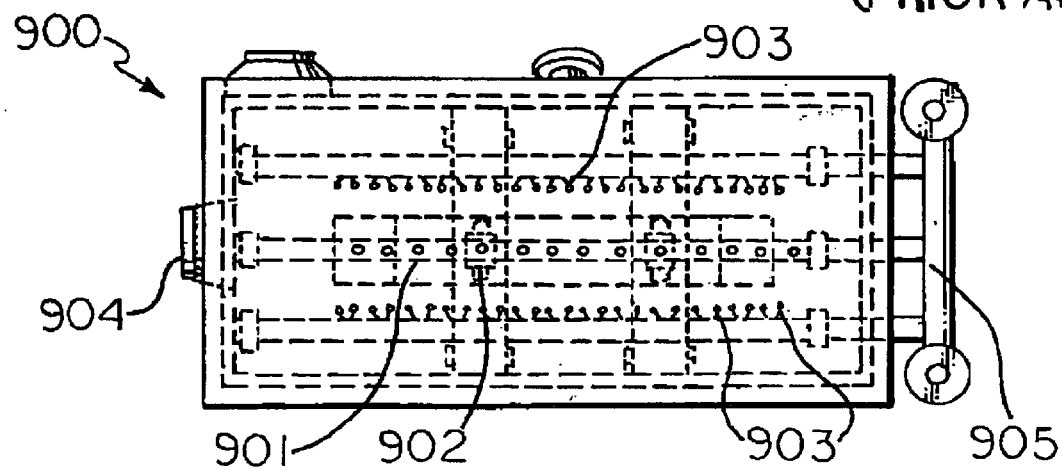
FIG. 9 is a plan view of a quench tank for use in the method of this invention.
Figure 10:
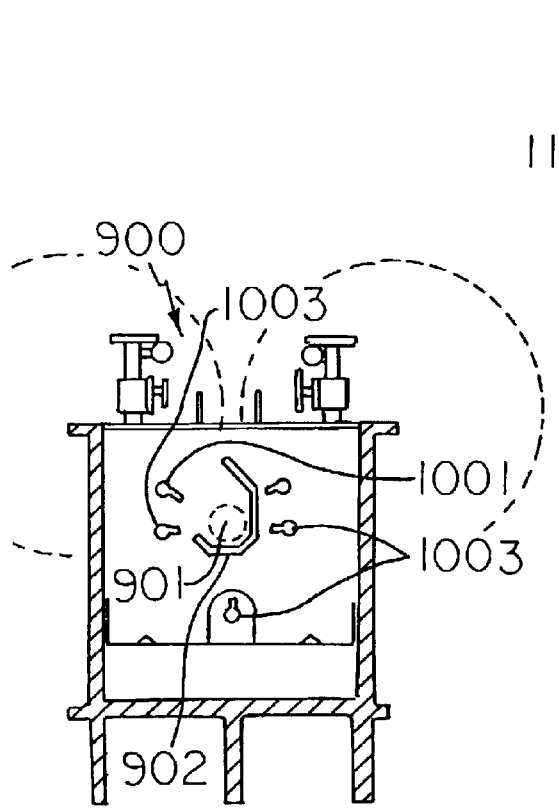
FIG. 10 is a section view of the quench tank in FIG. 9.

The heated polycrystalline silicon workpiece may be cooled in a quench tank. FIG. 9 is a plan view of an example of a quench tank 900 that may be used for cooling the heated polycrystalline silicon workpiece 901. The heated polycrystalline silicon workpiece 901 is placed in the quench tank 900 on supports 902. The supports 902 may be made of any material that will cause no (or low) contamination of the heated polycrystalline silicon workpiece 901. The heated polycrystalline silicon workpiece 901 is sprayed with a liquid from the nozzles 903. The liquid is fed from the inlet 904 to the outlet 905. FIG. 10 is a section view of the quench tank 900. FIG. 10 shows that the orientation of the sets of nozzles 1003 with respect to the heated polycrystalline silicon workpiece 901. The liquid may be fed through one set of nozzles 1003, or more than one set of nozzles 1003, at a time. The sets of nozzles 1003 may be arranged along pipes 1001. The pipes 1001 run parallel to the heated polycrystalline silicon workpiece 901. The pipes 1001 are arranged at 60°, 90°, 180°, and 270° from vertical. However, one skilled in the art would recognize that other arrangements of pipes and nozzles may be used.

After cooling, the workpiece may be cracked but still intact. Therefore, the cracked polycrystalline silicon workpiece may require a separator to extend the cracks and reduce the cracked polycrystalline silicon workpiece to a mixture of silicon pieces of varying sizes. Any separator that does not cause significant contamination of the mixture of silicon pieces may be used. The separator may be a mechanical, vibrational, or sonic separator. A suitable mechanical separator may comprise a hammer, such as a pneumatic, electric, magnetic, or hydraulic hammer.

Figure 11:
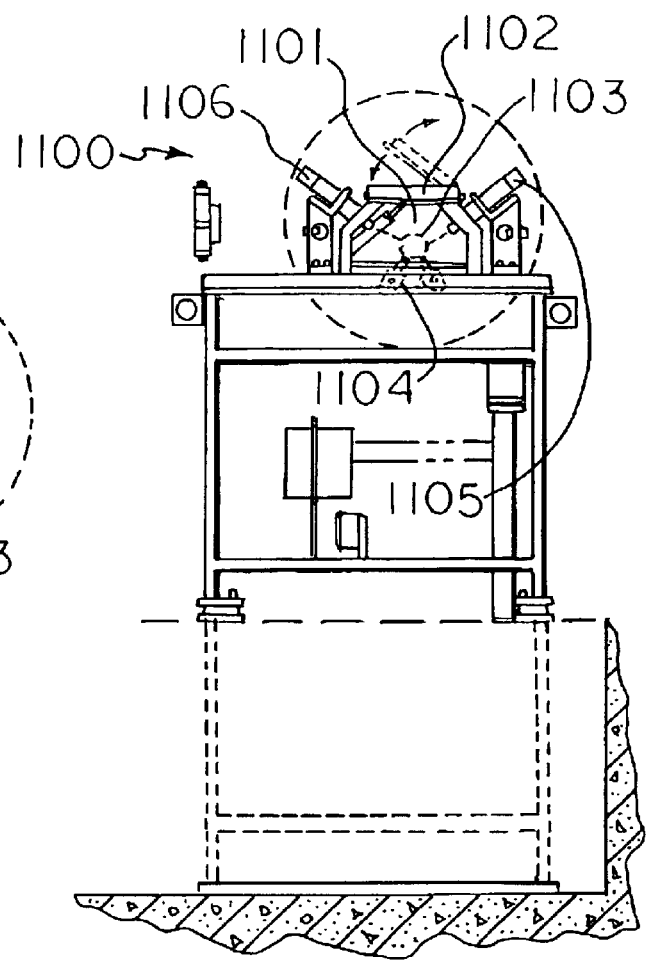
FIG. 11 is a section view of a mechanical separator for use in the method of this invention.
Figure 12:
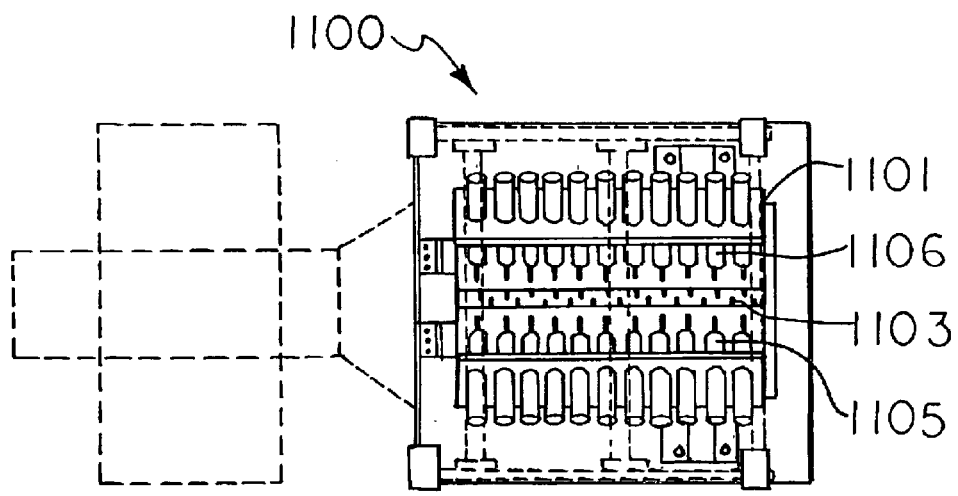
FIG. 12 is a top view of a pneumatic hammer chamber in the mechanical separator of FIG. 11.

FIG. 11 shows a section view of a suitable mechanical separator 1100 for use in this invention. The mechanical separator 1100 comprises a pneumatic hammer chamber 1101 with a lid 1102. A cracked polycrystalline silicon workpiece 1103 may be placed inside the chamber 1101 on supports 1104 made of a material that will cause no (or low) contamination of silicon. Arrays of pneumatic hammers 1105, 1106 are arranged parallel to the longitudinal axis of the workpiece 1103 and are positioned at an angle of 25° above horizontal. The hammers in one array 1105 may be offset from the hammers in another array 1106, as shown FIG. 12, which is a top view of the pneumatic hammer chamber 1101 in FIG. 11. However, one skilled in the art would recognize that the arrays of hammers may be inline or offset and that different arrangements of arrays and positions of arrays are possible.

Alternative methods for fragmenting the polycrystalline silicon workpiece include those disclosed in U.S. Pat. Nos. 4,871,117; 5,464,159; and 6,024,306; and JP 07-061808 A.

Sorting the Polycrystalline Silicon Pieces

The mixture of polycrystalline silicon pieces of varying sizes may be sorted into at least two size distributions by a variety of methods. The mixture may be sorted by hand or by machine. For example, the mixture of polycrystalline silicon pieces may be sorted using methods and apparatuses known in the art, such as the rotary silicon screen disclosed in U.S. Pat. No. 5,165,548. Alternatively, the mixture may be fed to a rotary indent classifier that sorts the mixture into at least two size distributions. The mixture may be fed to the classifier by any convenient means, such as a hopper, a chute, or a conveyor such as a bucket, belt, or vibratory conveyor.

The rotary indent classifier may comprise a disk having indents along the circumferential edge or a cylinder having indents along the circumferential edge. The indents along the circumferential edge of the cylinder may increase in size from a first end of the cylinder to a second end of the cylinder. The cylinder may be solid or hollow. Alternatively, the classifier may comprise an assembly comprising two or more arrays comprising one or more disks having indents along the circumferential edge. The indents may have different sizes from disk to disk or array to array.

The indents are sized to capture silicon pieces of a predetermined size or smaller and to reject silicon pieces of a size larger than the predetermined size. The classifier may comprise a single disk or cylinder having indents along the circumferential edge that are equally sized and the size is such that silicon pieces of a predetermined size or smaller are captured and silicon pieces of a larger size than the predetermined size are rejected. This forms two size distributions.

Alternatively, an assembly comprising a plurality of disks may be used, where the disks have indents of different sizes on different disks. The disks are arrayed such that the mixture of silicon pieces pass the disk having the smallest indents first and then pass by subsequent disks having indents in order of increasing size.

An example of such an assembly 100 including a plurality of disks 101 is shown in FIGS. 1 and 1*a*. In FIGS. 1 and 1*a*, the assembly 100 has four arrays 102*a*, 102*b*, 102*c*, and 102*d* of disks 101 having indents 103 along the circumferential edges 104 thereof. Multiple indent disks 101 are arranged along a shaft 105 to form arrays 102*a*–*d*, with each array end blocked by a plate 106. Indent disks 101 and plates 106 are held in position relative to each other on shaft 105 by means of securing rods 107, which extend the longitudinal length of the assembly 100.

The number of indents 103 in the circumferential edge of each disk 101 may be maximized to facilitate efficient separation of the mixture of silicon pieces. The disks 101 forming each of arrays 102*a*–*d* are sized to capture silicon pieces of a predetermined size or smaller and to reject silicon pieces of a size larger than the predetermined size. The depth of each indent 103 may be 40 to 70 percent of the width of the indent, alternatively 55 to 65 percent on the same basis. The thickness of each disk 101 may be selected such that indent length is 100 to 120 percent of the width of the indent, alternatively 100 to 110 percent on the same basis. Each indent 103 is shaped as half a cylinder (e.g., a cylinder sliced through its longitudinal axis).

Alternatively, a cylinder having indents formed along the circumferential edge, where the indents are positioned along the longitudinal length of the cylinder so as to increase in size from a first end of the cylinder to a second end of the cylinder, may be used. The indents effect differential separation of the mixture of silicon pieces by size as the mixture passes along the length of the cylinder.

Figure 2:
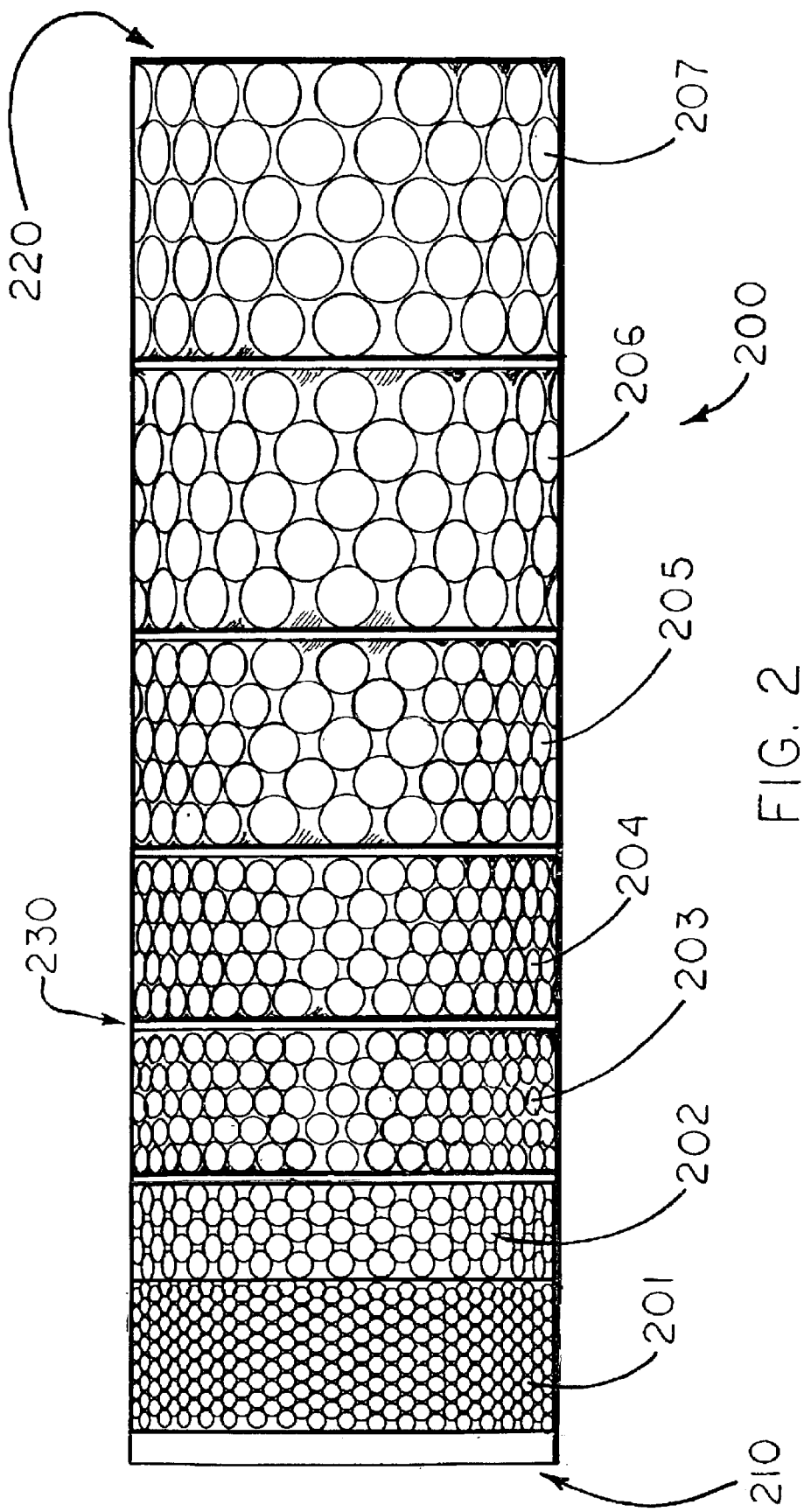
FIG. 2 is a front view of a cylinder 200 for use in a rotary indent classifier according to this invention.

An example of such a cylinder is shown in FIG. 2. In FIG. 2, the cylinder 200 has a first end 210, a second end 220, and a circumferential edge 230 therebetween. At the first end 210, the cylinder 200 has a first set of indents 201 arrayed along the circumferential edge of the cylinder 200. Each indent 201 has a diameter of one-half inch at the surface of the cylinder 200, and each indent 201 extends inward in the shape of half an ellipsoid. There are fifteen rows of indents

201. The rows of indents 201 are offset from one another. The cylinder 200 then has a second set of indents 202 adjacent to the first set of indents 201. Each of the indents 202 has a diameter of one inch at the surface of the cylinder 200, and each indent 202 extends inward in the shape of half an ellipsoid. There are five rows of indents 202. The rows of indents 202 are offset from one another. The cylinder 200 has a third set of indents 203 adjacent to the second set of indents 202. Each of the indents 203 has a diameter of one and one-half inches at the surface of the cylinder, and each indent 203 extends inward in the shape of half an ellipsoid. There are five rows of indents 203. The rows of indents 203 are offset from one another. The cylinder 200 has a fourth set of indents 204 adjacent to the third set of indents 203. Each of the indents 204 has a diameter of two inches at the surface of the cylinder, and each indent 204 extends inward in the shape of half an ellipsoid. There are five rows of indents 204. The rows of indents 204 are offset from one another. The cylinder 200 has a fifth set of indents 205 adjacent to the fourth set of indents 204. Each of the indents 205 has a diameter of two and one-half inches at the surface of the cylinder, and each indent 205 extends inward in the shape of half an ellipsoid. There are five rows of indents 205. The rows of indents 205 are offset from one another. The cylinder 200 has a sixth set of indents 206 adjacent to the fifth set of indents 205. Each of the indents 206 has a diameter of three inches at the surface of the cylinder, and each indent 206 extends inward in the shape of half an ellipsoid. There are five rows of indents 206. The rows of indents 206 are offset from one another. The cylinder 200 has a seventh set of indents 207 adjacent to the sixth set of indents 206. Each of the indents 207 has a diameter of three and one-half inches at the surface of the cylinder, and each indent 207 extends inward in the shape of half an ellipsoid. There are five rows of indents 207. The rows of indents 207 are offset from one another. Each set of indents is spaced one-half inch from the next set of indents.

The number of indents in the circumference of the each disk or cylinder is not critical, but may be maximized to facilitate efficient separation of the mixture of silicon pieces. Offsetting rows of indents may be done to maximize the number of indents. The shape of the indent may be, for example, cubic, cylindrical, half-cylindrical, ellipsoidal, half-ellipsoidal, or wedge-shaped. The depth of each indent may be 40 to 70% of the width of the indent measured at the circumferential edge, alternatively 55 to 65% on the same basis. One skilled in the art would be able to vary the number of indents, size of indents, spacing of indents, and number of sets or arrays of indents without undue experimentation.

Figure 3:
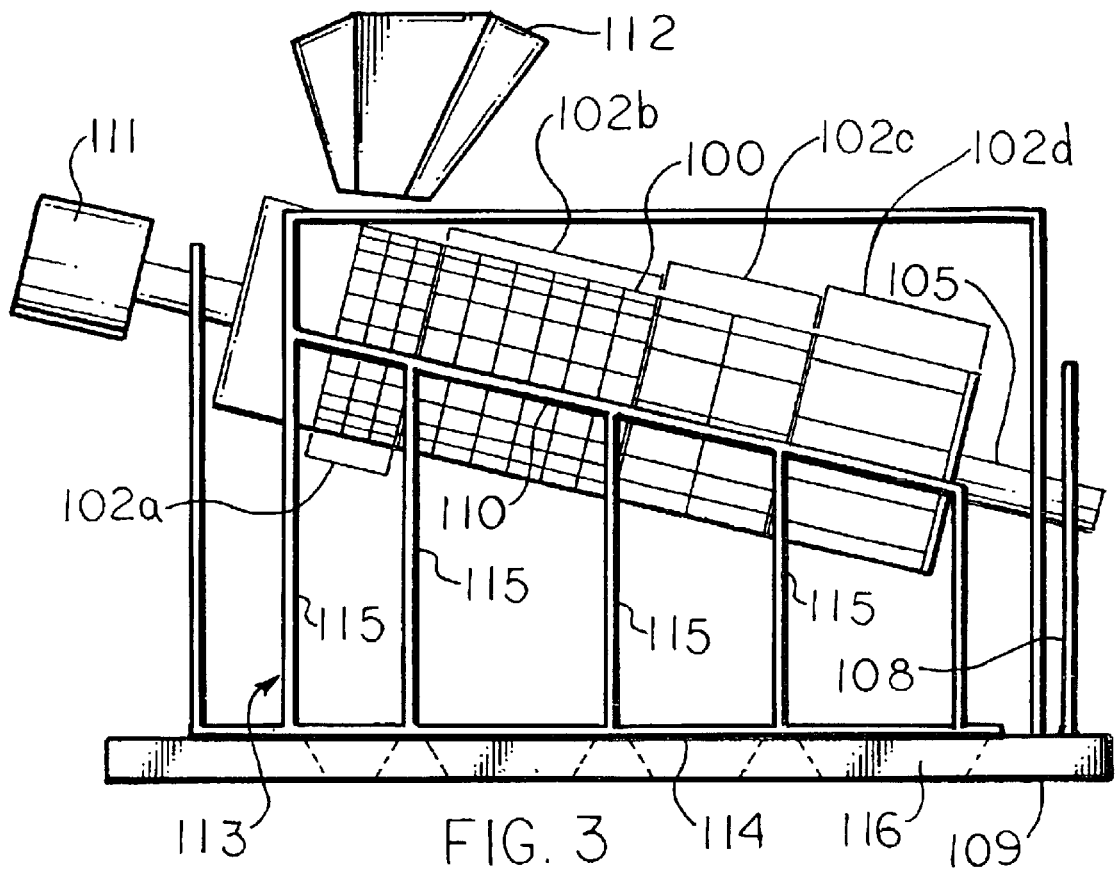
FIG. 3 is a front view of a rotary indent classifier according to this invention and including the assembly 100 of FIG. 1.

FIG. 3 shows a rotary indent classifier including the assembly 100 shown in FIG. 1. The ends of shaft 105 are rotationally affixed to a support 108, which rests on a base 109. The means of rotationally attaching shaft 105 to support 108 may be by standard bearings. The assembly 100 may be positioned in supports 108 such that the assembly 100 is at an incline of 5 to 20 degrees, alternatively 10 to 12 degrees above horizontal. The slope of the assembly 100 is positioned to facilitate the movement by gravity of a mixture of silicon pieces along slide plate 110. Supports 108 may be adjustable in height to facilitate change of the slope. Attached to the upper-end of shaft 105 is drive mechanism 111 for imparting rotational energy to the assembly 100. The rotational energy may be supplied by any convenient means such as electric motor, or pneumatic or hydraulic drive. Drive mechanism 111 may be connected to shaft 105 directly or by any convenient means such as belt, chain, reduction gear box, or combinations thereof. The assembly 100 may be rotated at a speed sufficient to provide a tangential velocity of 15 to 32 centimeters per second.

Feed distributor 112 is positioned at the upper end of the assembly 100. The mixture of silicon pieces may be fed by means of feed distributor 112 to array 102*a* to start the separation process. The shape of feed distributor 112 is not critical and may be a chute as shown in FIG. 3 or any other convenient design for feeding pieces of material to a rotating assembly, including but not limited to a hopper, a conveyor, a slide plate, or a combination thereof.

In FIG. 3, the assembly 100 is shown positioned within a collection container 113 comprising outer walls 114 and partition walls 115. Partition walls 115 separate the collection container 113 into a number of chambers to segregate the silicon pieces captured by each of arrays 102*a–d*. Also positioned in the collection container on an axis generally parallel to shaft 105 is slide plate 110. A slide plate 110 may be positioned on each side of the assembly 100. Slide plate 110 functions to allow gravitational movement of the mixture of silicon pieces along the length of the assembly 100. Slide plate 110 may be statically fixed or may be held in such manner as to allow vibration or movement to facilitate the movement of the silicon pieces down its length. One skilled in the art would recognize that assembly 100 need not be positioned in an integral container apparatus as shown, but may have separate collection containers positioned beneath each array 102*a–d*. Bottom container wall 114 and base 109 have located therein occludable ports 116 for removing the sorted silicon pieces from the chambers.

Figure 4:
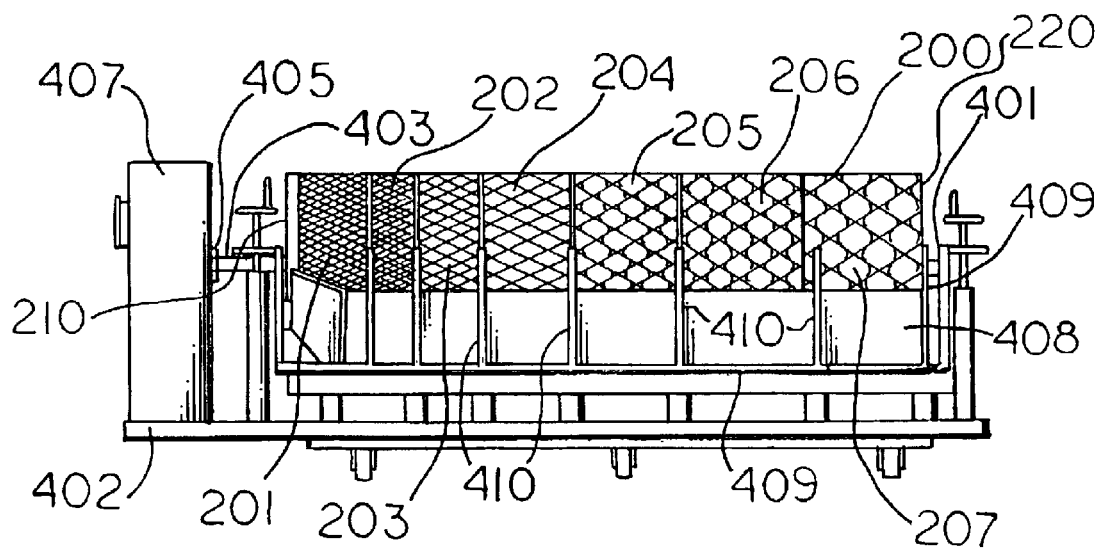
FIG. 4 is a front view of a rotary indent classifier according to this invention and including the cylinder 200 of FIG. 2.
Figure 5:
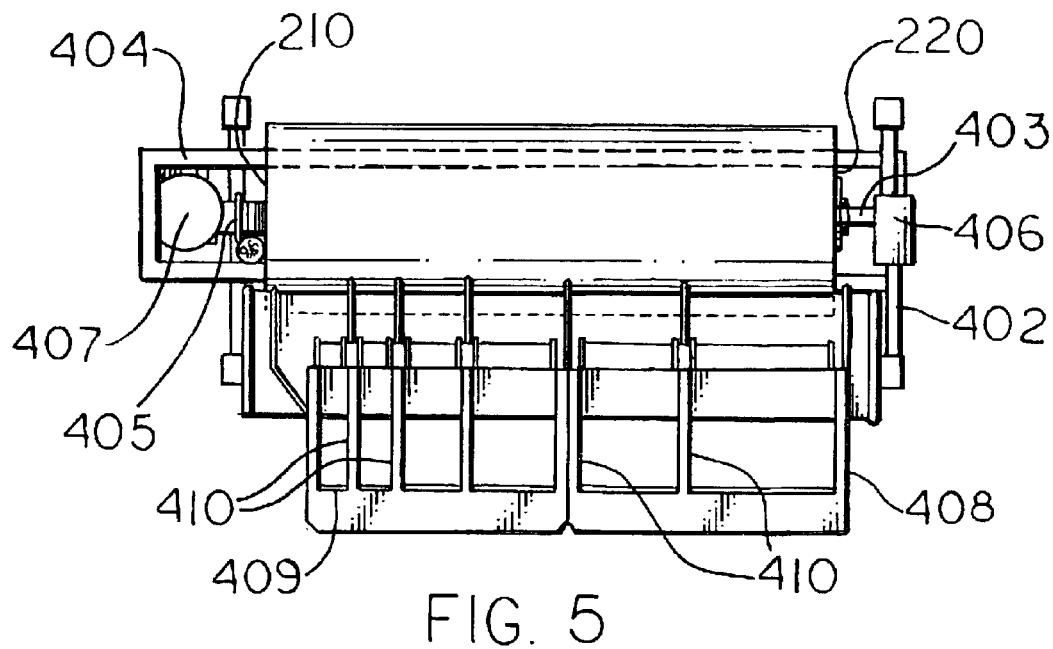
FIG. 5 is a plan view of the rotary indent classifier in FIG. 4.
Figure 6:
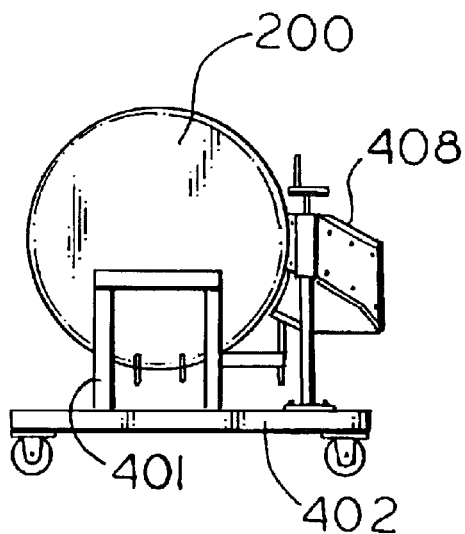
FIG. 6 is a left side view of the rotary indent classifier in FIG. 4.
Figure 7:
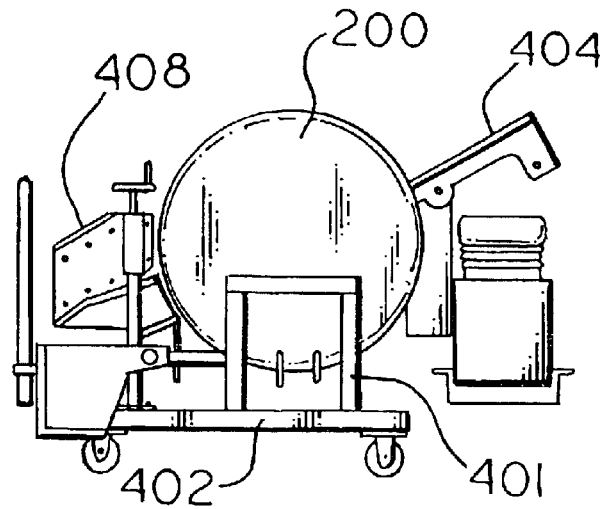
FIG. 7 is a right side view of the rotary indent classifier in FIG. 4.

FIGS. 4, 5, 6, and 7 show a rotary indent classifier 400 including the cylinder 200 shown in FIG. 2. FIG. 4 shows a front view of the rotary indent classifier 400. FIG. 5 shows a plan view of the rotary indent classifier 400. FIG. 6 shows a left side view of the rotary indent classifier 400. FIG. 7 shows a right side view of the rotary indent classifier 400. The cylinder 200 has a shaft 403 extending through the center of the longitudinal length of the cylinder 200. The cylinder 200 is rotationally mounted to a support 401 by the shaft 403. The support 401 rests on a base 402. The means of rotationally attaching shaft 403 to support 401 may be by standard bearings. The cylinder 200 may be positioned in supports 401 such that the cylinder 200 slopes at an incline of 0 to 20 degrees, alternatively 5 to 12 degrees above horizontal. The slope of the cylinder 200 is positioned to facilitate the movement of a mixture of silicon pieces along conveyor 404. Supports 401 may be adjustable in height to facilitate change of the slope. Attached to the first end 405 of shaft 403 is drive mechanism 407 for imparting rotational energy to the cylinder 200. The rotational energy may be supplied by any convenient means such as electric motor, or pneumatic or hydraulic drive. Drive mechanism 407 may be connected to shaft 403 directly or by any convenient means such as a belt, chain, reduction gear box, or combinations thereof. Alternatively, one skilled in the art would recognize that the drive mechanism may be connected directly to the cylinder by any convenient means, such as those described above. The cylinder 200 may be rotated at a speed sufficient to provide a tangential velocity of 15 to 32 centimeters per second.

Conveyor 404 begins at the first end 210 of the cylinder 200 and runs toward the second end 220 of the cylinder 200. The mixture of silicon pieces may be fed by means of conveyor 404 to the first end 210 of the cylinder 200 to start the separation process. The conveyor 404 runs longitudinally adjacent the cylinder 200 and conveys the mixture of silicon pieces along the length of the cylinder 200 from the first end 210 to the second end 220. The type of conveyor 404 is not critical and may be a vibratory conveyor as shown in FIG. 4 or any other convenient design, including but not limited to a bucket conveyor or a belt conveyor, for feeding pieces of material to a rotating assembly. One skilled in the art would recognize that other designs could be used to convey the mixture of silicon pieces along the length of the cylinder 200, such as a hopper, chute, slide plate, or combinations thereof.

In FIG. 4, the cylinder 200 is shown positioned behind a collection container 408 comprising outer walls 409 and partition walls 410. Partition walls 410 separate the collection container 408 into a number of chambers to segregate the silicon pieces captured by each set of indents 201–207. One skilled in the art would recognize that cylinder 200 may alternatively have separate collection containers positioned beneath each set of indents 201–207.

The method and apparatus of this invention are useful for sorting a mixture of sizes of silicon pieces into two or more size distributions. The method is suitable for sorting semiconductor grade silicon pieces for use, for example, in a Czochralski-type process for making high purity monocrystalline silicon. The shapes of silicon pieces that may be sorted by the method and apparatus of this invention include, but are not limited to, chunk, chip, flake, bead, granular, and powder.

The particle size and weight distribution of the mixture of silicon pieces of varying sizes to be separated using the method depends on various factors including whether a fluidized bed reactor process is used to make the mixture of silicon pieces or whether a chemical vapor deposition process is used to prepare a polycrystalline silicon workpiece, the process used to fracture the polycrystalline silicon workpieces, and the final use of sorted the silicon pieces. However, a mixture of silicon pieces where up to 90% of the silicon pieces have a particle size of 0.1 to 150 mm may be used. Silicon pieces having particle size greater than 150 mm may be subjected to further fracturing before being fed or re-fed to the classifier.

The number of size distributions into which the mixture of silicon pieces is separated will depend on the requirements for end use of the silicon pieces. The mixture of silicon pieces is separated into at least two size distributions, alternatively at least three size distributions. For example, the mixture of silicon pieces may be separated into at least seven size distributions as follows: less than 10 mm, 10 to 25 mm, 25 to 45 mm, 45 to 75 mm, 75 to 100 mm, 100 to 150 mm, and larger than 150 mm. Optionally, pieces in one or more of the size distributions may be combined in any ratio to satisfy customer requirements.

The apparatuses disclosed herein may be constructed of standard engineering materials. Those components that do not contact the silicon may be constructed of suitable metals such as stainless steel, iron, aluminum, and plastics. Those components contacting the silicon impart no or low surface contamination to the silicon. Therefore, the components that contact silicon anywhere in the process may be constructed of such low contamination materials as ultra high molecular weight polyethylene (UHMWPE), polypropylene, perfluoroalkoxy resin (PFA), polyurethane (PU), polyvinylidene fluoride (PVDF), TEFLON®, tungsten carbide, silicon, and ceramic. Indent disks and cylinders may be PVDF, UHMWPE, or silicon.

Optional Cleaning Process

Silicon may optionally be cleaned by methods known in the art one or more times in the above process. For example, the silicon workpiece may be cleaned either before or after fracturing, either before or after sorting the mixture of silicon pieces of varying sizes into different size distributions, or combinations thereof.

For example, the silicon pieces may be cleaned by the process disclosed in U.S. Pat. No. 5,851,303, which comprises sequentially contacting the silicon pieces with gaseous hydrogen fluoride and then with an aqueous solution comprising at least one half percent hydrogen peroxide, and thereafter drying the broken rods. Alternatively, the silicon pieces may be surface cleaned by anisotropic etching as described in Canadian Patent No. 954425 or U.S. Pat. No. 4,971,654. Other methods for cleaning silicon include those disclosed in U.S. Pat. Nos. 5,753,567; 5,820,688; and 6,309,467.

EXAMPLES

These examples are intended to illustrate the invention to one skilled in the art and should not be interpreted as limiting the scope of the invention set forth in the claims.

Example 1

A polycrystalline silicon rod is prepared by a chemical vapor deposition process. The rod is approximately cylindrical in shape and weighs 15 to 25 Kg. The rod is heated to a temperature of 690 to 710° F. in the microwave cavity described above and shown in FIG. 8 (from Microwave Materials Technologies, Inc., of Knoxville, Tenn., U.S.A.). The heated rod is transferred to the spray quench apparatus described above and shown in FIGS. 9 and 10. The heated rod is sprayed with deionized water at ambient temperature from a plurality of nozzles. The heated rod is sprayed for 1 to 5 minutes, and surface temperature decreases to 125 to 175° F. The rod is cracked but still intact. The cracked rod is transferred to a mechanical separator described above and shown in FIGS. 11 and 12. The mechanical separator comprises a pneumatic hammer chamber. The cracked polycrystalline silicon rod is struck with a plurality of pneumatic hammers and fractures. The resulting mixture of silicon pieces is transferred to a vibratory conveyor.

The mixture is fed to the rotary intent classifier 400 in FIGS. 4–7 by the vibratory conveyor 404. The vibratory feeder vibrates intermittently at the resonance frequency of the mixture of silicon pieces and at lower frequencies to control the feed rate of the mixture of silicon pieces. The cylinder 200 rotates at a speed of 5 to 10 r.p.m. The mixture of silicon pieces is sorted into five size distributions and collected in the collection bins 408.

We claim:

1. A method comprising:
    feeding a mixture of silicon piece to a rotary indent classifier comprising a rotating disk having a circumferential edge with one or more indents sized to capture silicon pieces of a predetermined size or smaller and to reject silicon pieces of a size larger than the predetermined size, thereby separating the mixture of silicon pieces into at least two size distributions.

2. The method of claim 1, where the rotary indent classifier comprises more than one rotating disk, and where each rotating disk has one or more indents.

3. The method of claim 2, where the rotating disks are arrayed such that the first rotating disk has the smallest sized indents and the last rotating disk has the largest sized indents.

4. The method of claim 1, where more than one rotary indent classifier is used in series, and where each rotating disk has indents of different sizes.

5. A method comprising:
    (A) feeding a mixture of silicon pieces to a rotary indent classifier,
        where the rotary indent classifier comprises a rotating cylinder having a circumferential edge with indents arrayed in increasing size from a first end of the cylinder to a second end of the cylinder, where the silicon pieces have varying sizes,
where the indents are sized to capture silicon pieces of a predetermined size or smaller and to reject silicon pieces of a size larger than the predetermined size,
where the mixture of silicon pieces is fed to the first end of the cylinder, and
(B) conveying the mixture of silicon pieces along the length of the cylinder, thereby effecting separation of the mixture into a plurality of size distributions.

6. The method of claim 5, where step (A) is carried out using a conveyor selected from a vibratory conveyor, a bucket conveyor, a belt conveyor, or a hopper.

7. The method of claim 5, where step (B) is carried out using a conveyor selected from a vibratory conveyor, a bucket conveyor, a belt conveyor, or a hopper.

8. The method of claim 5, where each indent has a shape selected from cubic, cylindrical, half-cylindrical, ellipsoidal, half-ellipsoidal, or wedge.

9. A method comprising:
(1) fracturing a polycrystalline silicon workpiece into a mixture of polycrystalline silicon pieces, where the polycrystalline silicon pieces have varying sizes; and
(2) sorting the mixture of polycrystalline silicon pieces into at least two size distributions using a rotary indent classifier.

10. The method of claim 9, where step (1) is carried out by the steps of:
(i) heating the polycrystalline silicon workpiece to a temperature of 600 to 1400° F.,
(ii) spraying the product of step (i) with a fluid from a nozzle, and
(iii) extending cracks in the product of step (ii) with a separator.

11. The method of claim 10, where step (i) is carried out with laser, infra-red, or microwave energy.

12. The method of claim 10, where the fluid used step (ii) is selected from purified water, a solution of HF in water, or a solution of ammonium hydroxide in water.

13. The method of claim 10, where the separator used in step (iii) is selected from a mechanical, sonic, or vibrational separator.

14. The method of claim 9, further comprising (3) a washing step comprising washing the silicon either before or after fracturing in step (1), either before or after sorting into size distributions in step (2), or combinations thereof.

15. The method of claim 9, where the rotary indent classifier comprises a rotating disk having a circumferential edge with one or more indents sized to capture polycrystalline silicon pieces of a predetermined size or smaller and to reject polycrystalline silicon pieces of a size larger than the predetermined size.

16. The method of claim 9, where the rotary indent classifier comprises a rotating cylinder having a circumferential edge with indents arrayed in increasing size from a first end of the cylinder to a second end of the cylinder, where the indents are sized to capture silicon pieces of a predetermined size or smaller and to reject silicon pieces of a size larger than the predetermined size.

17. The method of claim 16, where the mixture of polycrystalline silicon pieces is fed to the first end of the cylinder and conveyed along the length of the cylinder, thereby effecting separation of the mixture into a plurality of size distributions.

18. A method comprising:
(1) fracturing a polycrystalline silicon workpiece into a mixture of polycrystalline silicon pieces, where the polycrystalline silicon pieces have varying sizes; and
(2) separating the mixture of polycrystalline silicon pieces into at least two size distributions;
wherein step (1) is carried out by a process comprising:
(i) heating the polycrystalline silicon workpiece to a temperature of 600 to 1400° F.,
(ii) spraying the product of step (i) with a fluid from a plurality of nozzles, and
(iii) extending cracks in the product of step (ii) with a separator.

19. The method of claim 18, where step (i) is carried out with laser, infra-red, or microwave energy.

20. The method of claim 18, where the polycrystalline silicon workpiece is heated to a temperature of 600 to 750° F.

21. The method of claim 18, where the fluid used step (ii) is selected from purified water, solutions of HF in water, or ammonium hydroxide in water.

22. The method of claim 18, where the nozzles are oriented to produce irregular shaped polycrystalline silicon pieces.

23. The method of claim 18, where the nozzles are oriented to produce wedge or pie shaped pieces.

24. The method of claim 18, where a type of nozzle is selected to produce a cone spray pattern.

25. The method of claim 18, where a type of nozzle is selected to produce a flat fan spray pattern.

26. The method of claim 18, where the separator used in step (iii) is selected from a mechanical, sonic, or vibrational separator.

27. The method of claim 18, where step (2) is carried out using a rotary indent classifier.

28. The method of claim 18, further comprising (3) a washing step comprising washing the silicon either before or after fracturing in step (1), either before or after sorting into mixtures with different size distributions in step (2), or combinations thereof.

29. The method of claim 18 where the mixture of polycrystalline silicon pieces is sorted into more than two size distribution and further comprising (3) mixing two or more of the size distributions to form a new size distribution to meet customer requirements.

30. A method comprising:
(1) preparing a polycrystalline silicon workpiece by a chemical vapor deposition process,
(2) fracturing the product of step (1) into a mixture of polycrystalline silicon pieces of varying sizes, and
(3) sorting the product of step (2) into at least two size distributions; with the proviso that
(A) step (2) is carried out by a process comprising
(i) heating the product of step (1) to a temperature of 600 to 1400° F.,
(ii) spraying the product of step (i) with a fluid from a plurality of nozzles, and
(iii) extending cracks in the product of step (ii) with a separator; or
(B) step (3) is carried out by using a rotary indent classifier; or
(C) both (A) and (B).

31. A method comprising:
(1) preparing a polycrystalline silicon workpiece by a fluidized bed reactor process,
(2) sorting the product of step (1) into at least two size distributions using a rotary indent classifier.

* * * * *